United States Patent [19]

Velenyi et al.

[11] 4,319,066

[45] Mar. 9, 1982

[54] PREPARATION OF ALKENYL AROMATIC COMPOUNDS

[75] Inventors: Louis J. Velenyi, Lyndhurst; Serge R. Dolhyj, Parma; Andrew S. Krupa, Twinsburg, all of Ohio

[73] Assignee: The Standard Oil Company, Cleveland, Ohio

[21] Appl. No.: 174,463

[22] Filed: Aug. 1, 1980

[51] Int. Cl.³ .............................................. C07C 1/00
[52] U.S. Cl. .................... 585/437; 570/201; 260/465 H; 260/465 K; 585/323; 585/357
[58] Field of Search ............... 585/437, 439, 445, 323; 570/201, 143; 260/465 H, 465 K

[56] References Cited

U.S. PATENT DOCUMENTS

| | | | |
|---|---|---|---|
| 1,541,176 | 6/1925 | Ostromislensky | 585/437 |
| 1,986,241 | 1/1935 | Wulff et al. | 585/445 |
| 2,310,762 | 2/1943 | Daumiller et al. | 585/437 |
| 2,407,373 | 9/1946 | Kearby | 585/445 |
| 3,387,053 | 6/1968 | Lee | 585/445 |
| 3,726,914 | 4/1973 | Engenbrecht et al. | 562/409 |

FOREIGN PATENT DOCUMENTS

| | | | |
|---|---|---|---|
| 486573 | 5/1938 | United Kingdom | 585/439 |
| 1098697 | 1/1968 | United Kingdom | 585/444 |

*Primary Examiner*—Delbert E. Gantz
*Assistant Examiner*—Joseph A. Boska
*Attorney, Agent, or Firm*—Gary R. Plotecher; Herbert D. Knudsen; Larry W. Evans

[57] ABSTRACT

Cyclohexenyl and alkenyl aromatic compounds, such as cyclohexene and styrene, are prepared by a process comprising contacting a corresponding cyclohexyl or alkyl aromatic carboxylic acid, such as cyclohexyl carboxylic acid or 2-phenyl propionic acid, with a decarboxylation catalyst of the formula $$M_a M'_b O_x$$

where
M is copper or a combination of copper and molybdenum, and
M' is at least one promoter element, such as a Group IA element.

10 Claims, No Drawings

PREPARATION OF ALKENYL AROMATIC COMPOUNDS

BACKGROUND OF THE INVENTION

1. Field of the Invention

This invention relates to the preparation of cyclohexenyl and alkenyl aromatic compounds. In one aspect, the invention relates to the decarboxylation with concurrent dehydrogenation of cyclohexane and alkyl aromatic carboxylic acids while in another aspect, the invention relates to the use of certain copper and copper-molybdenum oxide compositions as decarboxylation catalysts. In yet another aspect, the invention relates to a novel process for preparing styrene.

2. Description of the Prior Art

Various processes are known for decarboxylating a carboxylic acid. For example, Fenton, U.S. Pat. No. 3,530,198, teaches a liquid-phase preparation of olefins from carboxylic acids by a process comprising contacting the acid with a complex catalyst comprising a Group VIII noble metal and a biphyllic ligand. Daumiller et al. U.S. Pat. No. 2,310,762, teach the vapor-phase preparation of aromatic vinyl compounds from carboxylic esters of aryl-substituted aliphatic alcohols. Other similar processes are known but do not include a concurrent dehydrogenation of the starting material. For example, Horeau et al., U.S. Pat. No. 3,080,419, teach a liquid-phase decarboxylation without concurrent dehydrogenation of various indene compounds and Pine, U.S. Pat. No. 3,476,803, teaches the decarboxylation of carboxylic acids to organic compounds having one less carbon atom than the starting material by contacting the acid with an active form of a crystalline zeolite having the structure of faujasite.

For various reasons none of the above processes are entirely satisfactory. Consequently, there exists an interest in developing new processes for preparing various olefinic compounds by decarboxylating corresponding paraffinic carboxylic acids.

SUMMARY OF THE INVENTION

According to this invention, cyclohexenyl and alkenyl aromatic compounds are prepared by a process comprising contacting a corresponding cyclohexyl or alkyl aromatic carboxylic acid with a decarboxylation catalyst of the formula $$M_aM'_bO_x \qquad (I)$$

where

M is copper or a combination of copper and molybdenum;

M' is at least one of sodium, potassium, rubidium, cesium, chromium, phosphorus, a Group VIII metal, tin and bismuth;

a is a number of about 0.1 to 1;

b is a number of about 0.01 to 0.5; and x is the number of oxygen atoms determined by the valence requirements of the other elements present.

This process is characterized by a high conversion of the starting material and a good selectivity to the olefinic product.

DETAILED DESCRIPTION OF THE INVENTION

Reactants

The starting materials of this invention are cyclohexyl and alkyl aromatic compounds. Representative of these materials are compounds of the formulae

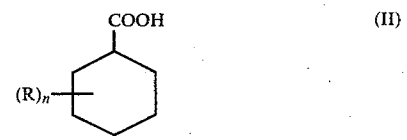

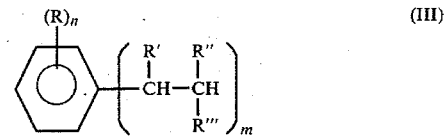

where

R is an inert substitutent, such as alkyl, aryl, halogen, nitrile, etc.;

R' is hydrogen, $C_1$–$C_4$ alkyl or a —COOH radical;

R" and R"' are independently R', phenyl or inertly-substituted phenyl radicals;

m is 1 or 2; and n is 0–4; with the provisoes that (i) one but only one of R', R" and R"' is a —COOH radical, and (ii) when either R" or R"' is a phenyl or an inertly-substituted phenyl radical, the other is neither a phenyl or an inertly-substituted phenyl radical.

"Inert-substituent" and like terms here mean that the substituents are essentially nonreactive with the starting materials, catalyst and products of the process at process conditions. Typical R Groups include $C_{1-4}$ alkyl radicals, phenyl radicals, chlorine, bromine, etc. "Inertly-substituted phenyl radicals" are phenyl radicals having at least one R substituent.

In formula III when m is 2, each radical within the parenthesis, i.e.

can be the same or different. Preferably n is 0, either R" or R"' is the —COOH radical and m is 1. Particularly preferred starting materials are cyclohexyl carboxylic acid (formula II where n is 0) and 2-phenyl propionic acid (formula III where n is 0, m is 1, R' is the —COOH radical, and R" and R"' are both hydrogen). Representative of other materials include compounds of the following formulae:

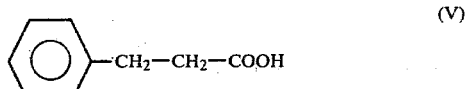

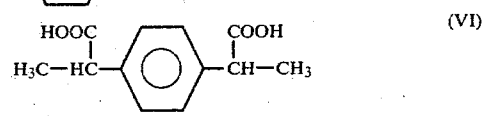

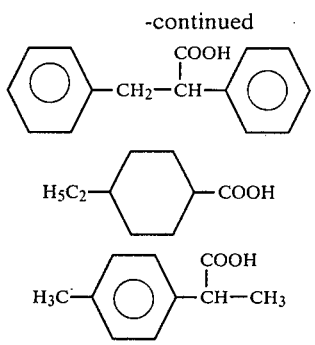

(VII)
(VIII)
(IX)

A feature common to all of these starting materials is that a double bond can be formed between the nonaromatic carbon atoms in the alpha and beta positions to one of the carboxylic acid groups.

Catalyst

The catalysts here used are compounds of formula I where M, M', a, b and x are as previously defined. Preferably, M is a combination of copper and molybdenum, M' is at least one of sodium, potassium, cesium, tin and bismuth, a is a number of about 0.5 to 0.9 and b is a number of about 0.1 to 0.3. More preferably, M' is either tin or a combination of bismuth and cesium. These catalysts can be used in either their 100% active form or diluted with other materials, e.g. loaded onto a carrier. If diluted, generally any carrier can be used with silica, alumina, silica-alumina, titania, zeolite, zirconia and the like all being exemplary. Carriers of alumina, silica and silica-alumina are preferred. If a support is used, the catalytic composition is generally present in an amount of at least about 5 weight percent, based on the combined weight of the support and the catalytic composition, and preferably in an amount of at least 20 weight percent.

The catalytic compositions of this invention can be prepared in any one of a number of different methods, the particular method employed being a matter of convenience. Typically, the catalysts are prepared by mixing the appropriate catalyst ingredients in the proper proportions in an aqueous mixture, drying the resulting aqueous slurry with or without a reducing agent, and calcining the product. The ingredients can be added in any order during the preparation procedure but preferably the metallic ingredients are mixed prior to the addition of the nonmetallic ingredients, e.g. phosphorus generally in the form of phosphoric acid. The ingredients employed can be the oxides, halides, nitrates, acetates or other salts of the particular metals or elements added and particularly preferred is the use of water soluble salts of the metal components. If a support is used, the material comprising the support may be incorporated into the catalyst along with the other ingredients or the catalytic composition can be coated and/or impregnated onto or into an inert core. After the catalyst ingredients have been combined to form an aqueous slurry, the slurry is taken to dryness and the dried solid obtained is heated in the presence of air, nitrogen or nitric oxide at temperatures between about 300° and about 420° C. This calcination can take place outside the catalytic reactor or an in situ activation can be utilized. Other methods of preparation are broadly taught in the art.

As taught by formula I, certain of the components can be combinations of two or more elements, e.g. M' can be a combination of cesium, phosphorus and bismuth. In such circumstances, the subscript value, b, represents the sum of the elements (e.g. for M', the sum of cesium, phosphorus and bismuth is equal to b which is less than or equal to about 0.5). The individual components of the subscript value, e.g. the subscript values for cesium, phosphorus and bismuth, can vary to convenience.

The exact structure or elemental arrangement of these catalysts is not known but the components are present in the form of their oxides or oxide complexes. However, compositions of formula I are known not to be a mere physical mixture of their components but rather unique entities where the individual components are chemically and/or physically bonded to one another.

Process Conditions

Heterogeneous catalysis is used in this invention, i.e. at reaction conditions the reactant is a gas or liquid while the catalyst is a solid. Any temperature and pressure at which the reactant is a gas or liquid and the catalyst is a solid can be employed but typically a temperature of at least about 250° C., and preferably at least about 375° C., is used. Practical considerations, such as economy, convenience and reactant, catalyst and product degradation, are the only limitations upon the maximum temperature that can be used but a typical maximum is about 550° C., and preferably about 500° C. Reaction pressure is important primarily as it relates to temperature and can thus vary from subatomospheric to superatmospheric.

If the reactant is a gas at reaction conditions, then it can be used by itself or diluted with a relatively inert gas. Representative diluent gases include nitrogen, argon, helium, carbon dioxide, steam, acetone vapor and the like. Likewise, if the reactant is a liquid at reaction conditions, then it can be used either alone or with a diluent, such as mixed hexanes and heptanes, cyclohexane, benzene, acetone, etc. If the reactant is a solid at room temperature, it is usually solubilized with a suitable solvent before exposure to the catalyst at reaction conditions.

Typically, the catalyst is employed in a fixed or ebullient-bed reactor where the reactant is passed over or through the catalyst.

Contact or residence time can also vary widely, depending upon such variables as the reactant, catalyst, reactor, temperature and pressure. Typical contact times range from a fraction of a second to more than several hours with preferred contact times between about 0.5 and 10 seconds.

Products

The products produced by this invention are olefinic compounds, specifically cyclohexenyl and alkenyl aromatic compounds. These compounds are formed by the concurrent decarboxylation and dehydrogenation (the latter of the nonaromatic carbon atoms alpha and beta to one of the or the carboxylic acid group) of the starting materials. For example, 2-phenyl propionic acid contacted with a catalyst of this invention produces styrene while cyclohexane carboxylic acid similarly contacted produces cyclohexene. By-products include carbon monoxide, carbon dioxide and water. The olefins produced by this invention are useful monomeric materials for the preparation of polymeric substances.

Manufacture of Styrene

In one embodiment of this invention, styrene is manufactured from benzene and propylene in a 3-step synthesis. Specifically, benzene is first alkylated with propylene to produce cumene. Cumene is then oxidized to 2-phenyl propionic acid which is in turn both decarboxylated and dehydrogenated by the method of this invention. The art is replete with methods for alkylating benzene and oxidizing cumene and any of these methods can be used in this embodiment. The conversion of 2-phenyl propionic acid by the method of this invention has been described above.

The following examples are illustrative embodiments of this invention. Per pass conversion (PPC) and selectivity were calculated using the following equations:

$$\% \, PPC = \frac{\text{Moles of Carbon in Desired Product} \times 100}{\text{Moles of Carbon Fed}} \quad \text{(X)}$$

$$\text{Selectivity} = \frac{\% \, PPC \text{ Desired Product} \times 100}{\% \, PPC \text{ of Total Product} \times \frac{n-1}{n}} \quad \text{(XI)}$$

where n = number of carbon atoms in starting material.

The correction in selectivity is required because the reactions necessarily involve the loss of one carbon as CO or $CO_2$.

SPECIFIC EMBODIMENTS

Example 1

A catalyst consisting of

| Component | Weight % |
|---|---|
| $Mo_{0.55} Cu_{0.45} Sn_{0.11} O_x$ | 30 |
| $SiO_2$ | 52.5 |
| $Al_2O_3$ | 17.5 | was prepared by dissolving 6.36 g of $Cu(CH_3COO)_2 \cdot H_2O$ in 800 cc of distilled water to yield a clear blue solution. To this solution was added 14.39 g of molybdenum trioxide in the form of ammonium heptamolybdate. The mixture was brought to boiling but did not obtain a complete solution. A light-green precipitate was present. To this mixture was added 3.01 g of stannous oxide powder and the entire mixture was brought to a boil for ½ hr after which 101.4 g of 41% colloidal silicon dioxide and 13.86 g of Dispal M alumina were added. The resulting mixture was then evaporated to a thick, light-green paste, dried for 4 hours at about 110° C. and the resulting hard, light green material was calcined for two hours at 380° C. in a muffle furnace. The final product was a very hard, light-green material which was ground to a 10-30 mesh (US Standard).

The catalyst was charged to a 20 cc down-flow, fixed-bed reactor. A feed of 50% cyclohexyl carboxylic acid and 50% acetone was then fed to the reactor, together with steam and nitrogen, at various temperatures and a product collected and anlyzed. The off-gas was passed through a cold acetone scrubber where the liquid products were retained. These liquid products were then quantitatively analyzed using an Hewlett-Packard gas chromatograph. Process conditions and results are reported in Table I.

TABLE I

Cyclohexylcarboxylic Acid to Cyclohexene
Catalyst: 30% $(Mo_{0.55} Cu_{0.45} Sn_{0.11} O_x)$ 52.5% $SiO_2$ 17.5% $Al_2O_3$

| Run | Temp (°C.) | Contact Time (sec.) | Feed Molar Ratio Acid: $N_2$: $H_2O$ | Per Pass Conversion to Cyclohexene | Selectivity |
|---|---|---|---|---|---|
| 1A. | 300 | 1.0 | 1:23:61 | 4.2 | 17.0 |
| 1B. | 400 | 0.8 | 1:23:61 | 28.4 | 50.4 |
| 1C. | 500 | 0.8 | 1:23:61 | 23.9 | 27.9 |

The data of Table I demonstrates both the relatively good conversion and selectivity of the carboxylic acid to the cycloalkene (cyclohexene).

EXAMPLE 2

Example 1 was repeated except 100% 2-phenyl propionic acid was substituted for the cyclohexyl carboxylic acid/acetone mixture and steam (water) was deleted from the feed mixture. The process conditions and results are reported in Table II.

TABLE II

2-Phenyl Propionic Acid to Styrene
Catalyst: 30% $(Mo_{0.55} Cu_{0.45} Sn_{0.11} O_x)$ 52.5% $SiO_2$ 17.5% $Al_2O_3$

| Run | Temp (°C.) | Contact Time (sec.) | Feed Molar Ratio Acid:$N_2$ | Per Pass Conversion to Styrene | Selectivity |
|---|---|---|---|---|---|
| 2A. | 400 | 3.1 | 1:38 | 72.1 | 81.1 |
| 2B. | 350 | 3.3 | 1:38 | 80.6 | 90.7 |
| 2C. | 300 | 3.8 | 1:38 | 57.3 | 98.9 |
| 2D. | 350 | 1.5 | 1:117 | 87.7 | 98.7 |
| 2E. | 350 | 1.6 | 1:117 | 96.8 | 97.3 |

The data of Table II demonstrate the efficacy of this invention in converting 2-phenyl propionic acid to styrene.

Example 3

The procedures of Example 1 and 2 were repeated except that a catalyst of the composition

| Component | Weight % |
|---|---|
| $Cs_{0.08} Mo_{0.96} P_{0.08} Bi_{0.04} Cu_{0.04}$ | 35 |
| Alundum ® (fused-alumina support) | 65 | was used. The catalyst was prepared by dissolving 51.3 g of $H_3Mo_{12}PO_4 \cdot 14H_2O$ in 250 ml of water. To this were added 1.23 g of copper acetate yielding a blue-green solution. To this solution was then added 1.59 g of bismuth trichloride/hydrochloric acid, the resulting solution was stirred and heated continuously for one hour and then titrated with ammonium hydroxide to a pH of about 5.4. Subsequently, 4.8 g of cesium nitrate was added and the stirring and heating was continued until a thick paste was obtained. The paste was then dried overnight in an oven at 110° C.

The dried catalyst was ground to <50 (US Standard) mesh and 26.9 g of the resulting powder was added in four portions to 50 g of ⅛ in. Alundum ® spheres which had been previously been treated with 2 g of water for 30 min. The treatment consisted of adding the water to the spheres with rolling to insure good water impregnation. A rolling procedure was then used to apply the dry powder to the wet catalyst support. When the coating was completed, the supported catalyst was dried overnight in an oven at 100° C. to yield a 35% active composition. This catalyst coating technique is more fully described in U.S. Pat. No. 4,077,912.

The results of the use of this catalyst are reported in Table III. 14 g (17.5 cc) of catalyst were employed.

TABLE III

2-Phenyl Propionic Acid to Styrene
Catalyst: 35% ($Cs_{0.08}$ $Mo_{0.96}$ $P_{0.08}$ $Bi_{0.04}$ $Cu_{0.04}$) on Alundum ®

| Run | Temp (°C.) | Contact Time (sec.) | Feed Molar Ratio Acid:N$_2$ | Per Pass Conversion to Styrene | Selectivity |
| --- | --- | --- | --- | --- | --- |
| 3A. | 350 | 1.3 | 1:17 | 23.4 | 97.9 |
| 3B. | 350 | 1.3 | 1:117 | 12.3 | 88.1 |
| 3C. | 350 | 1.2 | 1:117 | 40.1 | 97.2 |

Example 4

Example 1 was repeated except 2-phenyl propionic acid was substituted for cyclohexyl carboxylic acid. The 2-phenyl propionic acid was mixed with acetone to give an acid:acetone weight ratio of 1:3. The results are reported in Table IV.

TABLE IV

2-Phenyl Propionic Acid to Styrene
Catalyst: 30% ($Mo_{0.55}$ $Cu_{0.45}$ $Sn_{0.41}$ $O_x$) 52.5% $SiO_2$ 17.5% $Al_2O_3$

| Run | Temp (°C.) | Contact Time (sec.) | Feed Molar Ratio Acid:N$_2$:H$_2$O | Per Pass Conversion to Styrene | Selectivity |
| --- | --- | --- | --- | --- | --- |
| 4A. | 350 | 1.0 | 1:61:160 | 42.3 | 100.0 |
| 4B. | 450 | 0.8 | 1:61:160 | 61.7 | 94.6 |
| 4C. | 550 | 0.8 | 1:61:160 | 66.8 | 75.2 |
| 4D. | 500 | 0.8 | 1:61:160 | 21.6 | 24.3 |
| 4E. | 450 | 0.85 | 1:61:160 | 75.0 | 84.4 |

Example 5

Example 4 was repeated except that the 2-phenyl propionic acid was diluted with tetrahydronaphthalene. At 350° C., a contact time of 3.3 sec and a feed ratio of 1 part acid for every 50 parts nitrogen (no water), the normalized per pass conversion of acid to styrene was 44.8% with 50.4% selectivity. At 350° C., a contact time of 1 sec and a feed ratio of acid:nitrogen:water of 1:50:130, the normalized per pass conversion to styrene was 50.7% with a selectivity of 86.2%.

Comparison Example

The procedure of example 1 as again repeated except ⅛ in. Alundum ® spheres of 10/30 mesh (US Standard) were substituted as the catalyst. 100% (undiluted) 2-phenyl propionic acid was fed over 20 cc of catalyst at 350° C. and a contact time of 1.6 sec. A feed ratio of acid:nitrogen of 1:117 was used. The normalized per pass conversion to styrene was 0 and accordingly, the selectivity was 0. 95.6% of unconverted acid was recovered.

Although the invention has been described in considerable detail through the preceding examples, these examples are for the purpose of illustration only and it is understood that variations and modifications can be made by one skilled in the art without departing from the spirit and scope of the appended claims.

The claimed invention is:

1. A process for preparing an alkenyl aromatic compound, the process comprising contacting a corresponding alkyl aromatic carboxylic acid with a decarboxylation catalyst of the formula $$M_a M'_b O_x \qquad (I)$$

where
M is copper or a combination of copper and molybdenum;
M' is at least one of sodium, potassium, rubidium, cesium, chromium, phosphorus, a Group VIII metal, tin and bismuth;
a is a number of about 0.1 to 1;
b is a number of about 0.01 to 0.5; and
x is the number of oxygen atoms determined by the valence requirement of the other elements present.

2. The process of claim 1 where the carboxylic acid is of the formula $$(R)_n \text{---} \bigcirc \text{---} \left( \begin{array}{c} R' \quad R'' \\ | \quad | \\ -CH-CH- \\ | \\ R''' \end{array} \right)_m \qquad (III)$$

where
R is an inert substituent;
R' is hydrogen, $C_1$-$C_4$ alkyl or a —COOH radical;
R'' and R''' are independently R', phenyl or inertly-substituted phenyl radicals;
m is 1 or 2, and
n is 0–4; with the provisoes that
(i) one but only one of R', R'' and R''' is a —COOH radical, and
(ii) when either R'' or R''' is a phenyl or an inertly-substituted phenyl radical, the other is neither a phenyl or an inertly-substituted phenyl radical.

3. The process of claim 2 where m is 1 and n is 0.

4. The process of claim 3 conducted in the vapor phase.

5. A process for preparing an alkenyl aromatic compound, the process comprising contacting a corresponding alkyl aromatic carboxylic acid of the formula $$(R)_n \text{---} \bigcirc \text{---} \left( \begin{array}{c} R' \quad R'' \\ | \quad | \\ -CH-CH- \\ | \\ R''' \end{array} \right)_m \qquad (III)$$

where
R is an inert substituent;
R' is hydrogen, $C_1$-$C_4$ alkyl or a —COOH radical;
R'' and R''' are independently R', phenyl or inertly-substituted phenyl radicals;
m is 1 or 2, and
n is 0–4; with the provisoes that
(i) one but only one of R', R'' and R''' is a —COOH radical, and
(ii) when either R'' and R''' is a phenyl or an inertly-substituted phenyl radical, the other is neither a phenyl or an inertly-substituted phenyl radical;
with a decarboxylation catalyst of the formula $$M_a M'_b O_x \qquad (I)$$

where

M is a combination of copper and molbydenum;

M' is at least one of sodium, potassium, cesium, tin and bismuth;

a is a number of about 0.1 to 1;

b is a number of about 0.01 to 0.5; and x is the number of oxygen atoms determined by the valence requirement of the other elements present.

6. The process of claim 5 where M' is tin or a combination of bismuth and cesium and b is a number of about 0.1 to about 0.3.

7. The process of claim 6 conducted in the vapor phase and in the presence of a diluent gas.

8. The process of claim 7 where the diluent gas is steam or acetone vapor.

9. The process of claim 8 where the carboxylic acid is 2-phenyl propionic acid.

10. A process for the manufacture of styrene, the process comprising:
  (1) alkylating benzene with propylene to produce cumene,
  (2) oxidizing cumene to 2-phenyl propionic acid, and
  (3) concurrently decarboxylating and dehydrogenating the 2-phenyl priopionic acid by the process of claim 5.

* * * * *